(12) United States Patent
Taylor et al.

(10) Patent No.: US 11,429,918 B2
(45) Date of Patent: Aug. 30, 2022

(54) ROBOT DELIVERIES BASED ON PERSONAL DATA

(71) Applicant: Hewlett-Packard Development Company, L.P., Spring, TX (US)

(72) Inventors: Stacie Taylor, Corvallis, OR (US); Will Allen, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 39 days.

(21) Appl. No.: 16/611,946

(22) PCT Filed: Jun. 26, 2017

(86) PCT No.: PCT/US2017/039176
§ 371 (c)(1),
(2) Date: Nov. 8, 2019

(87) PCT Pub. No.: WO2019/004992
PCT Pub. Date: Jan. 3, 2019

(65) Prior Publication Data
US 2021/0081888 A1  Mar. 18, 2021

(51) Int. Cl.
*G06Q 10/08* (2012.01)
*G16H 20/30* (2018.01)
*G06Q 50/30* (2012.01)

(52) U.S. Cl.
CPC ..... *G06Q 10/0832* (2013.01); *G06Q 10/0833* (2013.01); *G06Q 50/30* (2013.01); *G16H 20/30* (2018.01)

(58) Field of Classification Search
CPC ........... G06Q 10/0832; G06Q 10/0833; G06Q 50/30; G16H 20/30
See application file for complete search history.

(56) References Cited

U.S. PATENT DOCUMENTS 7,261,511 B2   8/2007 Felder et al.
7,822,547 B2 * 10/2010 Lindroos ................ G01C 22/00
                                                        340/995.19

(Continued)

FOREIGN PATENT DOCUMENTS

CN    205799529      12/2016
WO    WO-2016130856   8/2016
WO    WO-2017064202   4/2017

OTHER PUBLICATIONS

Fujitsu Office Delivery Robot, 2009, http://www.roboticstoday.com/robots/fujitsu-office-delivery-robot-description, Retrieved on Apr. 21, 2017, 2 pages.

(Continued)

*Primary Examiner* — Daniel Vetter
*Assistant Examiner* — Christopher Gomez
(74) *Attorney, Agent, or Firm* — Tong, Rea, Bently & Kim LLC (57) ABSTRACT

In example implementations, a robot that makes deliveries based on personal data and a method for performing the same is provided. The method includes receiving, by a processor of the robot, a request to deliver an item to a recipient. Personal data associated with the recipient is checked and a location to deliver the item to the recipient is determined based on the personal data. The location for delivery of the item is then transmitted to an endpoint device of the recipient.

14 Claims, 4 Drawing Sheets

(56) References Cited

U.S. PATENT DOCUMENTS

| | | |
|---|---|---|
| 8,179,418 B2 | 5/2012 | Wright et al. |
| 8,583,282 B2 | 11/2013 | Angle et al. |
| 2009/0012802 A1* | 1/2009 | Pinney .................. G06Q 10/08 705/330 |
| 2012/0173448 A1* | 7/2012 | Rademaker .......... G06Q 10/083 705/338 |
| 2013/0066591 A1* | 3/2013 | Kinsbourne ......... G01C 22/006 702/160 |
| 2013/0204410 A1 | 8/2013 | Napolitano |
| 2014/0147819 A1* | 5/2014 | Cricchio ................ G16H 20/70 434/238 |
| 2014/0189016 A1* | 7/2014 | Goldsmith .............. H04L 67/22 709/205 |
| 2014/0254896 A1 | 9/2014 | Zhou et al. |
| 2015/0006005 A1* | 1/2015 | Yu .......................... G06Q 50/28 701/22 |
| 2015/0160014 A1* | 6/2015 | Hewitt ................... G01C 21/20 701/522 |
| 2015/0377635 A1 | 12/2015 | Beaurepaire et al. |
| 2017/0024538 A1* | 1/2017 | Siddiqui ............ G06Q 30/0207 |
| 2017/0031449 A1* | 2/2017 | Karsten ................ G06F 3/0346 |
| 2018/0024554 A1* | 1/2018 | Brady ............... G06Q 10/0833 701/23 |

OTHER PUBLICATIONS

White, Matthew et al. "Assistive/Socially Assistive Robotic Platform for Therapy and Recovery: Patient Perspectives," Int'l Journal of Telemed and Applications, vol. 2013 (2013), Article ID 948087, 6 pages.

* cited by examiner

ROBOT DELIVERIES BASED ON PERSONAL DATA

BACKGROUND

Enterprises and work places are becoming more aware of the personal fitness and health of employees. Office environments can lead to long stationary hours for employees, which can lead to health problems. The increase of health problems for employees can lead to increased health costs for the enterprise.

Certain companies have recognized this issue and taken steps to try and improve the fitness and health of their employees. For example, some companies provide step counters to employees to encourage employees to get up and move around throughout the day.

However, countering the steps taken by companies to improve the health of employees are workplace robots. The robots may be deployed in a building to deliver items to the employees and the employees may not have to walk to the supply cabinet to get certain items. As a result, movement and activity of the employees may actually be reduced due to the robots.

DETAILED DESCRIPTION

Examples of robot deliveries based on personal data are described herein. As discussed above, robots are being used in companies to deliver items to employees. The robots bring items directly to the employee at his or her desk. However, the use robots to deliver items may have a negative impact on the health of employees as employees move less throughout the day. As noted above, a direct correlation may exist between costs to the company and health of the employees.

Examples are described herein where the robot can be modified to provide deliveries in a way to improve the fitness of the employees. For example, personal data associated with an employee may be used to determine a delivery location of a requested item. The employee may then meet the robot at the location to obtain the item.

The personal data may include data such as fitness goals, calendar information, route preferences, and the like that allow the robot, or a controller in communication with the robot, to calculate the best location to deliver the item. For example, rather than delivering an item to the desk or office of an employee, the robot may deliver an item to a different building on a campus of the company. The different building may be selected to cause the user to walk and meet fitness goals within an allotted time before a meeting that is on the employees calendar. Thus, the robot deliveries based on personal data may help improve the overall fitness and health of employees within a company or enterprise.

Figure 1:
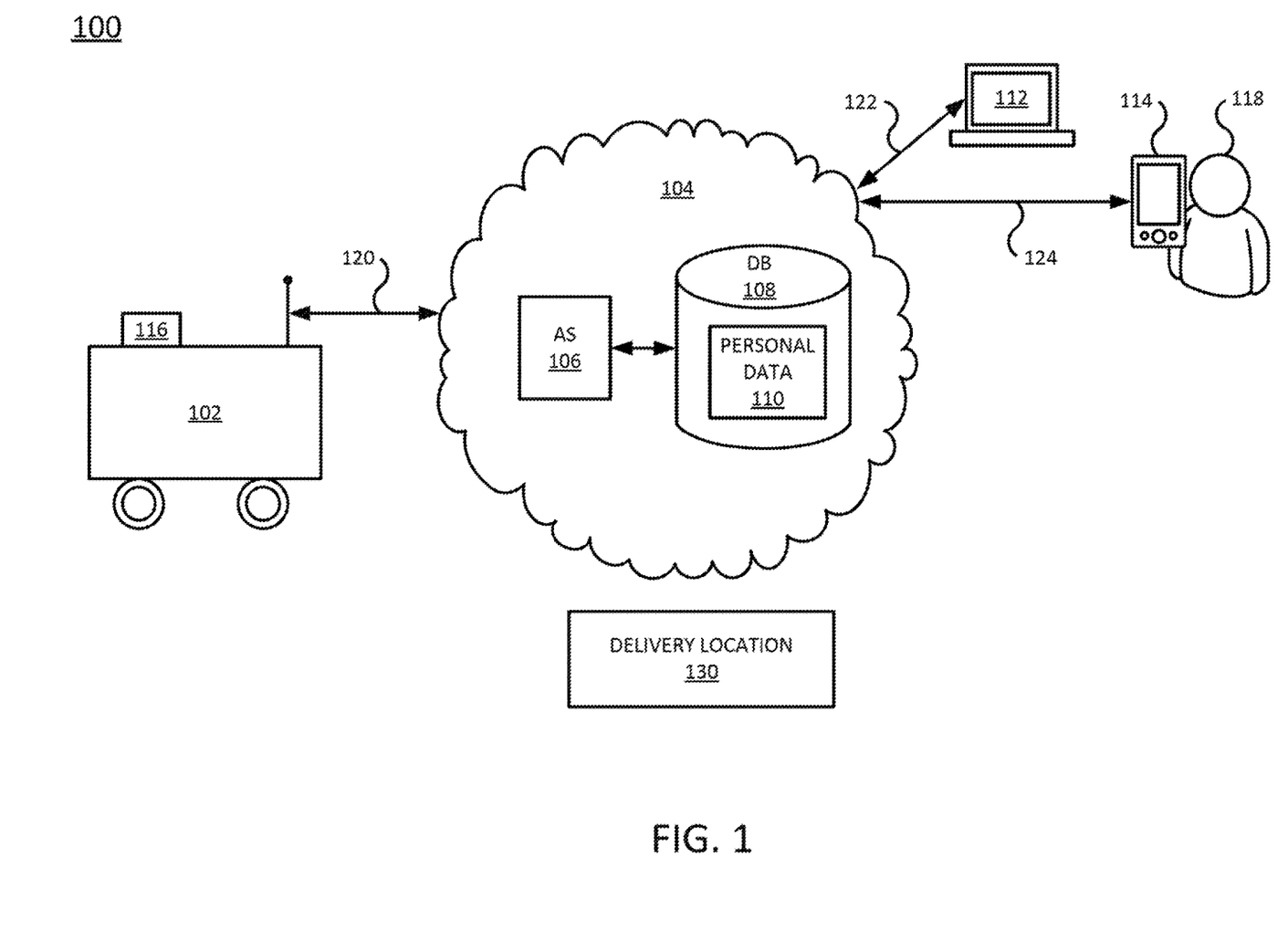
FIG. 1 is a block diagram of a system of the present disclosure.

FIG. 1 illustrates a block diagram of a system 100 of the present disclosure. In one example, the system 100 may include a robot 102, an Internet protocol (IP) network 104, an endpoint device 112 and a user 118. In one example, the robot 102 may be a delivery robot that is programmed to help meet exercise goals of the user 118. It should be noted that although a single robot 102 is illustrated in FIG. 1, that the system 100 may include any number of robots 102.

In one example, the robot 102 may deliver an item 116 that is requested by the user 118. For example, the user 118 may be an employee of an enterprise, or a company, and may request to have office supplies delivered. However, rather than having the robot 102 deliver the item 116 directly to the office of the user 118, the robot 102 may determine a delivery location 130 away from the location of the user 118.

In one example, the delivery location 130 may be a location that is different than the location of the user 118. The delivery location 130 may be a different floor, a different building on a campus of the company, an outdoor location, and the like, that causes the user 118 to walk to the delivery location 130. As a result, the user 118 may walk to the delivery location 130 to meet his or her exercise goals throughout the day.

The IP network 104 may include an application server (AS) 106 in communication with a database (DB) 108. It should be noted that the IP network 104 has been simplified for ease of explanation and may include additional network elements not shown (e.g., gateways, routers, firewalls, border elements, network controllers, and the like).

In one example, the DB 108 may include personal data 110. The personal data 110 may include information obtained from the endpoint device 112 of the user 118. For example, the personal data 110 may include exercise goals of the user 118 that are used by the robot 102 to determine the delivery location 130, as discussed in further detail below. The personal data 110 may include a daily step goal, a current number of steps taken, a daily calorie burn goal, a personal calendar, a route preference, and the like.

The personal data 110 may be entered by the user 118 via the endpoint device 112. In some examples, the personal data 110 may be automatically obtained via the communication path 122. For example, the AS 106 may access a personal calendar or a work calendar on a calendar application of the endpoint device 112. In another example, the AS 106 may be in communication with a mobile endpoint device 114 that may track daily steps taken, daily calories burned, and the like. For example, the mobile endpoint device 114 may transmit information to the AS 106 and the information may be stored in the personal data 110 in the DB 108. The information may be used by the AS 106 to determine how many more steps the user 118 may take to reach daily exercise goals, and other similar information to determine the delivery location 130.

In one example, the robot 102 may establish a communication path 120 to the AS 106 via the IP network 104. The AS 106 may transmit the personal data 110 to the robot 102 to determine the delivery location 130 based on the personal data 110, as discussed in further detail below. For example, the robot 102 may consider upcoming appointments in the work calendar of the user 118, a number of additional steps to meet the daily step goal and daily calorie burn goal, route preferences of the user 118, and the like to determine the delivery location 130.

In one example, the AS 106 may coordinate communication between the robot 102 and the endpoint device 112. For example, the robot 102 may establish the communication path 120 and the endpoint device 112 may establish a communication path 122 to the IP network 104. The AS 106 may then establish a communication path for the robot 102 to directly communicate with the endpoint device 112. In one example, the user 118 may submit a request for the item 116 to be delivered by the robot 102 over the communication path 122 via the endpoint device 112. The AS 106 may communicate the request to the robot 102. The robot 102 may then directly communicate with the endpoint device 112 via the communication path that is established between the robot 102 and the endpoint device 112 by the AS 106.

In one example, the user 118 may also have the mobile endpoint device 114. The mobile endpoint device 114 may establish a communication path 124 to the IP network 104. The AS 106 may then establish a communication path for the robot 102 to communicate directly with the mobile endpoint device 114. The delivery location 130 determined by the robot 102 may be transmitted to the endpoint device 112 or the mobile endpoint device 114 via the communication paths that are established between the robot 102 and the endpoint device 112 or the mobile endpoint device 114. In addition, as discussed below, other types of information (e.g., location data, update information, notifications, and the like) can be transmitted directly to the mobile endpoint device 114 as the user 118 is moving to the delivery location 130 via the direct communication path to the mobile endpoint device 114.

In one example, the endpoint device 112 may be any type of computing device such as a desktop computer, a laptop computer, a tablet computer, a smart phone, a wearable device, and the like. In some instances when the endpoint device 112 is a laptop computer, a tablet computer, a smart phone, or a wearable device, the endpoint device 112 and the mobile endpoint device 114 may be the same device. In other instances, the user 118 may initially communicate with the robot 102 via the endpoint device 112 that is a desktop computer in an office, and then communicate with the robot 102 via the mobile endpoint device 114 while the user 118 is moving. Although a single endpoint device 112, a single mobile endpoint device 114 and a single user 118 is illustrated in FIG. 1, it should be noted that any number of endpoint devices 112, mobile endpoint devices 114 and users 118 may be deployed in the system 100.

Figure 2:
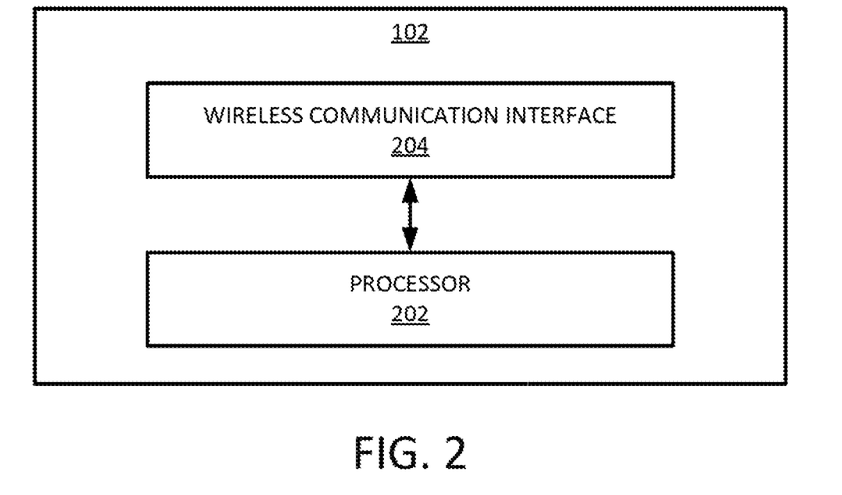
FIG. 2 is a block diagram of a robot of the present disclosure.

FIG. 2 illustrates a block diagram of the robot 102. In one example, the robot 102 may include a wireless communication interface 204 and a processor 202 in communication with the wireless communication interface 204. The wireless communication interface 204 may be a Wi-Fi interface, wireless network card, and the like that allows the robot 102 to establish and communicate over the communication path 120 with the IP network 104.

The robot 102 may receive a request for delivery of the item 116 to the user 118, or employee, via the wireless communication interface 204. As noted above, the robot 102 may establish a first communication path (e.g., the communication path 120) with the AS 106. The AS 106 may receive the initial request for delivery and the AS 106 may then forward the request to the robot 102 via the first communication path. The AS 106 may then establish a second communication path directly between the robot 102 and the endpoint device 112, or the mobile endpoint device 114.

In one example, the robot 102 may respond to the request with a notification asking whether the user 118 would like to activate an exercise setting. If the user 118 responds with a "no," then the robot 102 may deliver the item 116 directly to the user 118 at the current location of the user 118. If the user 118 responds with a "yes," then the robot 102 may activate an exercise mode and calculate, or determine, the delivery location 130 that is away from, or remote from, the current location of the user 118.

To calculate the delivery location 130, the processor 202 may obtain the personal data 110 associated with the user 118. The personal data 110 may be used by the processor 202 of the robot 102 to determine the delivery location 130 to deliver the item 116 to the user 118. The processor 202 may then transmit the delivery location 130 to the endpoint device 112, or the mobile endpoint device 114, of the user 118 via the wireless communication interface 204 and the second communication path. The delivery location 130 may also include a route map that the user 118 may follow based on the personal data 130 or route preferences of the user 118, as discussed below.

The processor 202 may determine the delivery location 130 to meet exercise goals of the user 118 stored in the personal data 110 and based on preferences and calendar information also stored in the personal data 110. For example, processor 202 may determine a daily step goal of the user 118 stored in the personal data 110. The processor 202 may also determine how many steps the user 118 has currently taken based on data stored in the personal data 110. The processor 202 may know an average distance traveled per step of the user 118.

The average distance traveled may be based on historical data of the user such as daily steps taken and total distance travelled that may collected by the mobile endpoint device 114 and transmitted to the AS 106. In another example, the user 118 may provide the average distance per step manually to the AS 106 via the endpoint device 112. The processor 202 may then select the delivery location 130 that is at a distance far enough away from the current location of the user 118 that will cause the user 118 to take enough steps to meet his or her daily step goal.

In another example, the processor 202 may determine the delivery location 130 based on more sophisticated calculations. For example, the processor 202 may check the personal calendar and the work calendar of the user 118. The processor 202 may check to see that the user 118 has a meeting that begins in 15 minutes from the current time. Thus, using the average distance traveled information for a single day described above, the processor 202 may calculate an average walking speed of the user 118. The processor 202 may find a location that can be travelled within the amount of time (e.g., 15 minutes) before the meeting begins.

In one example, the processor 202 may see that the user 118 has "workout," "gym day," or some other language indicating that the user 118 will be exercising after work, or later in the day. The processor 202 may determine that the deficit between the current steps taken and the daily step goal of the user 118 does not have to be met by the delivery location 130. In other words, the processor 202 may assume that the user 118 will be taken some additional steps later in the day based on the personal calendar and select the delivery location 130 that may not meet the step deficit to reach the daily step goal of the user 118.

In another example, the processor 202 may select the delivery location 130 based on a route preference of the user 118 stored in the personal data 110. For example, the user 118 may prefer an outdoor location, a route that takes the user 118 outdoors and to a different building, a route that takes the user all indoors without going outside, and the like.

In one example, the user 118 may have a preference of delivery location based on the current weather (e.g., temperature and precipitation). For example, the user 118 may set a preference in the personal data 110 that when the weather is below 80 degrees Fahrenheit (° F.) and there is no rain or snow, the user would like the delivery location 130 to be outside. The robot 102 may access a weather status on the AS 106 via the wireless communication interface 204 to get a current weather status and calculate the delivery location 130 accordingly.

Figure 3:
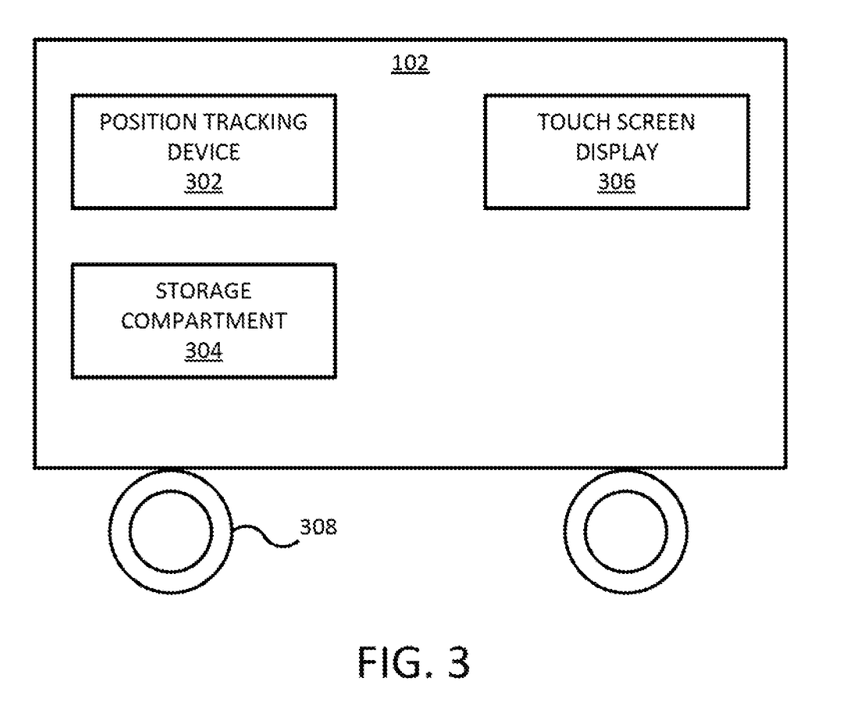
FIG. 3 is another block diagram of the robot of the present disclosure.

FIG. 3 illustrates another block diagram of the robot 102. The robot 102 may also include a position tracking device 302, a storage compartment 304, a touch screen display 306, and a movement mechanism 308. In one example, the position tracking device 302, actuated mechanisms of the storage compartment 304, the touch screen display 306 and the movement mechanism 308 may be in communication with the processor 202.

The position tracking device 302 may be a global positioning system (GPS) radio, sensors that detect movement of the robot 102, and the like. The position tracking device 302 may determine and/or collect location data of the robot 102. The processor 202 may control movement of the robot 102 to the delivery location 130 via the location data collected by the position tracking device 302. In one example, the location data of the robot 102 may be used in conjunction with other data (e.g., current speed of the robot 102, distance to the delivery location 130, and the like) to provide updates to the endpoint device 112 or the mobile endpoint device 114. For example, the robot 102 may transmit a notification to the endpoint device 112, or the mobile endpoint device 114, of the user 118 to leave based on the current location of the robot 102 and the estimated time of travel of the user 118 to the delivery location 130. In another example, the robot 102 may transmit an update with an estimated time of arrival to the delivery location 130 based on the current location of the robot 102 and the estimated distance left to travel.

In one example, the mobile endpoint device 114 of the user 118 may also have a position tracking device (not shown). The location data (e.g., GPS location data) of the mobile endpoint device 114 may be collected and transmitted to the robot 102 as the user 118 is walking to the delivery location 130. The robot 102 may use the location data from the mobile endpoint device 114 to track the movement and speed of the user 118. Based on the movement and speed of the user 118, the robot 102 may transmit notifications or updates to the user 118.

For example, as noted above, the robot 102 may have determined the delivery location 130 based amount a time before a meeting that is scheduled in the work calendar of the user 118. The robot 102 may determine that the user 118 is moving too slow and may be late to the meeting. The robot 102 may transmit a notification to the mobile endpoint device 114 of the user 118 that notifies the user 118 to walk faster, or increase a pace of movement, based on tracking the user 118 with the location data from the mobile endpoint device 114.

In another example, the robot 102 may detect that the user 118 has deviated from a calculated route to the delivery location 130 and provide directions to return to the selected route. The robot 102 may use the location data received from the mobile endpoint device 114 to calculate an estimated time of arrival (ETA) and periodically provide ETA information to the user 118 via the mobile endpoint device 114.

In one example, the storage compartment 304 may store the item 116 for transportation. For example, the storage compartment 304 may be internal with an actuated door or enclosure, be a mechanical arm or clasp on top of the robot 102, and the like.

In one example, the touch screen display 306 may provide an interface for the user 118. For example, the user 118 may provide input to the robot 102 that the item was successfully delivered at the delivery location 130 when the item 116 is obtained by the user 118. The touch screen display 306 may provide updated personal data to the user 118. For example, based on information regarding the number of steps taken (e.g., via the mobile endpoint device 114 communicating with the AS 106) from the AS 106, the robot 102 may display to the user 118 a current number of steps taken, a number of remaining steps to reach a daily step goal, an updated number of calories burned, and so forth.

In one example, the touch screen display 306 may also display additional information, such as game results, to the user. For example, the exercise goals of the user 118 may be tied in with a game hosted by the AS 106 for users or employees of a company. The amount of points awarded to the user 118, or added to a current point total of the user 118, may be based on how far the user 118 has traveled. The points may be displayed to the user 118 via the touch screen display 306 after confirmation is received that the user 118 has obtained the item 116. The touch screen display 306 may communicate with the AS 106 to obtain updated point totals for the user 118, updated standings relative to other users or employees of the company, and the like.

In one example, the movement mechanism 308 may include wheels, treads, and the like. The movement mechanism 308 may be controlled by the processor 202 to move the robot 202.

Figure 4:
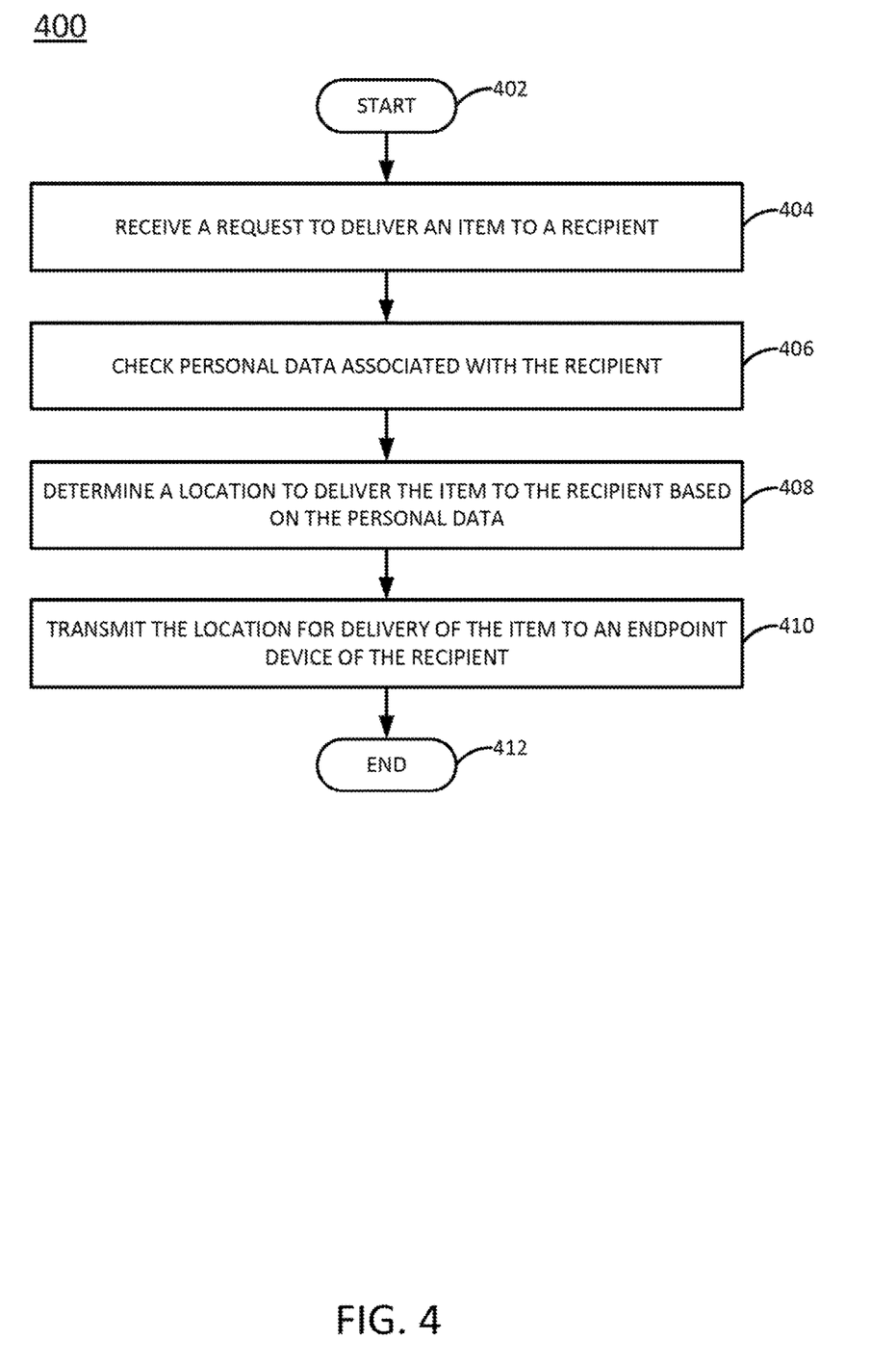
FIG. 4 is a flow chart of an example method for delivering an item based on personal data of the present disclosure.

FIG. 4 illustrates a flow diagram of an example method 400 for delivering an item based on personal data. In one example, the method 400 may be performed by the robot 102 or an apparatus 500 described below and illustrated in FIG. 5.

At block 402, the method 400 begins. At block 404, the method 400 receives a request to deliver an item to a recipient. For example, an employee may be the recipient and request delivery of an office item.

At block 406, the method 400 checks personal data associated with the recipient. For example, as discussed above, various information may be stored in the personal data. The personal data may include exercise goals of the recipient (e.g., current steps taken, a daily step goal, current calories burned, a daily calorie burn goal, and the like), personal calendar information, work calendar information, route preferences, and the like.

In one example, the personal data may be stored in a database and in communication with an application server in a communication network. The communication network may control and manage the operation of robots that are deployed at an enterprise location or campus. The robot may receive the request and then access the personal data stored in the database via a communication path established with the application server.

At block 408, the method 400 determines a location to deliver the item to the recipient based on the personal data. The location may be a delivery location that is located remotely from the recipient. In other words, the location may be a location that is different than a current location of the recipient.

The location may be determined based on personal data such as, a number of steps to meet a daily step goal, a number of calories to be burned to meet a daily calorie burn goal, upcoming meetings found in a work calendar, additional exercise or activities found in a personal calendar, route preferences, weather preferences, and the like. In one example, the different types of personal data may be weighted for determining the delivery location. For example, the user may weigh the number of steps to meet a daily step goal higher than the number of calories to be burned, information in the personal calendar, and the like. For example, the user may know that he or she sometimes may skip a workout that is found in his or her personal calendar. Thus, the user may weigh meeting the daily step goal higher than information found in the personal calendar.

At block 410, the method 400 transmits the location for delivery of the item to an endpoint device of the recipient. The location for delivery that is transmitted may include a route map to the location based on the personal data or route preference of the recipient.

The location for delivery may be transmitted to the endpoint device used by the recipient to send the request for delivery or a different mobile endpoint device. For example, the recipient may use his or her mobile endpoint device while walking to the delivery location.

As noted above, the robot may interact with the user via notifications and updates sent to the mobile endpoint device as the user is walking to the delivery location. The user may arrive to the delivery location and confirm that the item was delivered via a user interface of the robot (e.g., a touch screen display). In one example, updated personal data may be displayed to the recipient or transmitted to the endpoint device of the recipient after confirmation that the item was delivered.

In one example, a game, or a competitive reward system between employees of the enterprise, may be associated with the robot to further help the recipient meet his or her exercise goals. For example, points may be added to a score of the recipient and standings may be displayed to the recipient. At block 412, the method 400 ends.

Figure 5:
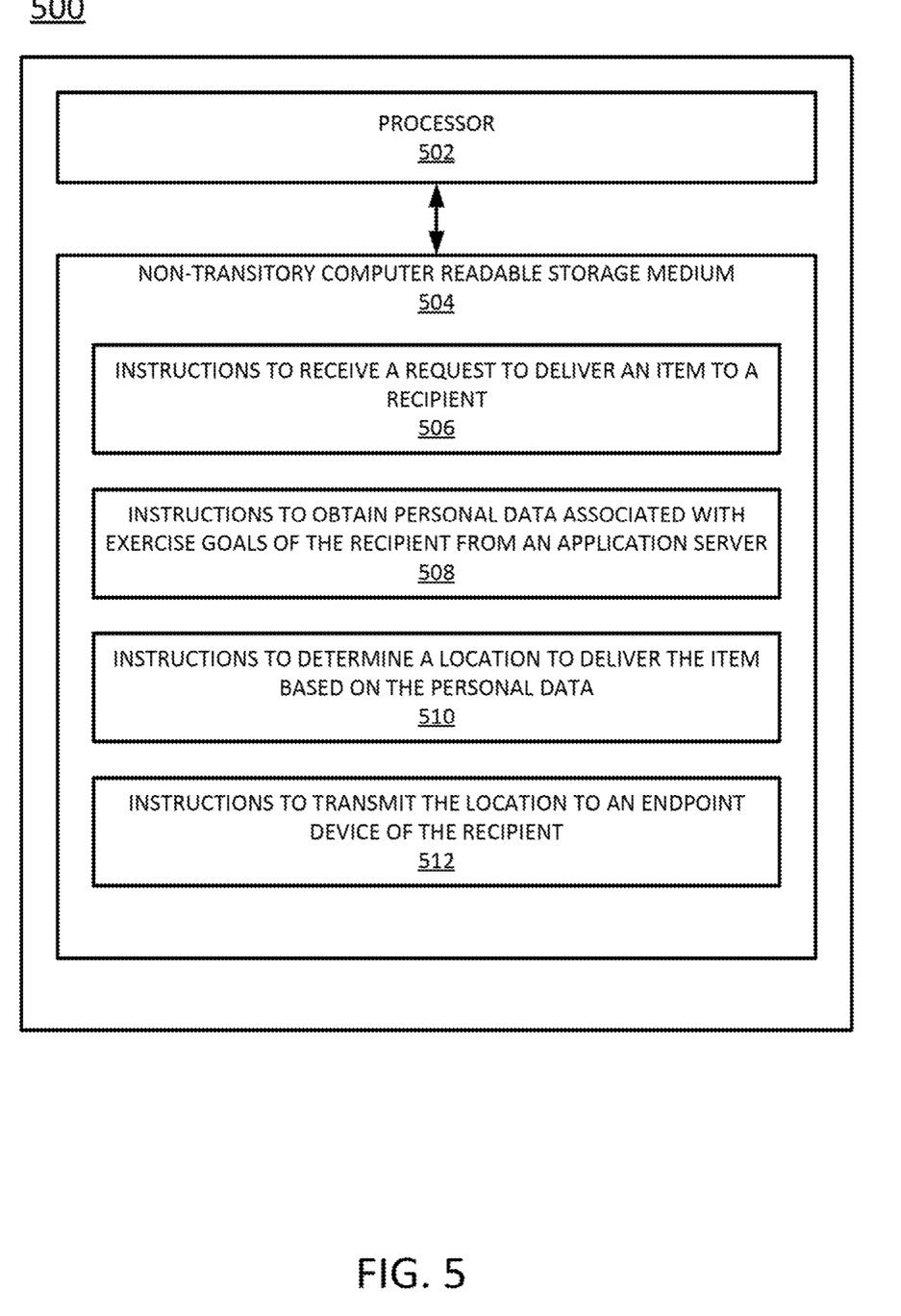
FIG. 5 is a block diagram of an example non-transitory computer readable medium storing instructions executed by a processor of the present disclosure.

FIG. 5 illustrates an example of an apparatus 500. In one example, the apparatus 500 may be the robot 102. In one example, the apparatus 500 may include a processor 502 and a non-transitory computer readable storage medium 504. The non-transitory computer readable storage medium 504 may include instructions 506, 508, 510 and 512 that when executed by the processor 502, cause the processor 502 to perform various functions.

In one example, the instructions may include instructions 506 to receive a request to deliver an item to a recipient. The instructions 508 may include instructions to obtain personal data associated with exercise goals of the recipient from an application server. The instructions 510 may include instructions to determine a location to deliver the item based on the personal data. The instructions 512 may include instructions to transmit the location to an endpoint device of the recipient.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A method, comprising:
receiving, by a processor of a robot, a request to deliver an item to a recipient;
checking, by the processor, personal data associated with the recipient, wherein the personal data comprises a daily step goal, a current number of steps taken, and a personal calendar or a work calendar;
determining, by the processor, a location to deliver the item to the recipient based on the personal data, wherein the location is different from a current location of the recipient and located a distance that is far enough from the current location of the recipient for the recipient to meet the daily step goal, wherein the determining the location comprises:
determining, by the processor, an amount of time before a meeting begins on the personal calendar or the work calendar;
determining, by the processor, an average distance traveled per step of the recipient;
determining, by the processor, an average walking speed of the recipient based on an average distance traveled per day by the recipient;
calculating, by the processor, a distance from the current location of the recipient to deliver the item based on the amount of time, the average distance traveled per step of the recipient, the average walking speed, and a remaining number of steps of the daily step goal such that the location to deliver the item can be travelled within the amount of time before the meeting begins; and
determining, by the processor, the location to deliver the item based on the distance that is calculated;
transmitting, by the processor, the location for delivery of the item to an endpoint device of the recipient; and
controlling, by the processor, movement of the robot to the location via a position tracking device of the robot to collect location data of the robot.

2. The method of claim 1, wherein the personal data further comprises a daily calorie burn goal and a route preference.

3. The method of claim 1, wherein the location includes a route map based on a route preference of the recipient.

4. The method of claim 1, comprising:
confirming, by the processor, that the item is delivered to the recipient; and
updating, by the processor, the personal data associated with the recipient.

5. The method of claim 4, comprising:
adding, by the processor, points to a score associated with the recipient, wherein the score is associated with a competitive reward system that includes employees of an enterprise.

6. The method of claim 1, comprising:
establishing, by the processor, a communication path to a step tracking mobile endpoint device of the recipient;
tracking, by the processor, movement of the recipient based on location data received from the step tracking mobile endpoint device.

7. The method of claim 6, comprising:
transmitting, by the processor, a notification to the endpoint device of the recipient to increase a pace of movement of the recipient based on the tracking.

8. The method of claim 6, comprising:
transmitting, by the processor, a notification to the endpoint device of the recipient that the recipient is deviating from a route map to the location.

9. A robot, comprising:
a wireless communication interface to establish a first communication path to an application server and a second communication path to an endpoint device to receive a request for delivery of an item to an employee;
a processor in communication with the wireless communication interface, the processor to:
obtain personal data associated with the employee via the first communication path to the application server to determine a location to deliver the item to the employee, wherein the personal data comprises a daily step goal, a current number of steps taken, and a personal calendar or a work calendar, wherein the location is different from a current location of the employee and located a distance that is far enough from the current location of the employee for the recipient to meet the daily step goal, wherein the location is determined by determining an amount of time before a meeting begins on the personal calendar or the work calendar, determining an average distance traveled per step of the employee, determining an average walking speed of the employee based on an average distance traveled per day by the employee, calculating a distance from the current location of the employee to deliver the item based on the amount of time, the average distance traveled per step of the employee, the average walking speed, and a remaining number of steps of the daily step goal such that the location to deliver the item can be travelled within the amount of time before the meeting begins, and determining the location to deliver the item based on the distance that is calculated; and transmit the location to an endpoint device of the employee via the second communication path to the endpoint device; and a position tracking device to collect location data to determine a location of the robot, wherein the processor controls movement of the robot to the location based on the location data.

10. The robot of claim 9, comprising:
a storage compartment to hold the item that is requested.

11. The robot of claim 9, comprising:
a touch screen display to receive confirmation that the item was delivered to the employee and to display updated personal data to the employee.

12. A non-transitory computer readable storage medium encoded with instructions executable by a processor of a robot, the non-transitory computer-readable storage medium comprising:

instructions to receive a request to deliver an item to a recipient;

instructions to obtain personal data associated with exercise goals of the recipient from an application server, wherein the personal data comprises a daily step goal, a current number of steps taken, and a personal calendar or a work calendar;

instructions to determine a location to deliver the item based on the personal data, wherein the location is different from a current location of the recipient and located a distance that is far enough from the current location of the recipient for the recipient to meet the daily step goal, wherein the instructions to determine the location comprises:

instructions to determine an amount of time before a meeting begins on the personal calendar or the work calendar;

instructions to determine an average distance traveled per step of the recipient;

instructions to determine an average walking speed of the recipient based on an average distance traveled per day by the recipient;

instructions to calculate a distance from the current location of the recipient to deliver the item based on the amount of time, the average distance traveled per step of the recipient, the average walking speed, and a remaining number of steps of the daily step goal such that the location to deliver the item can be travelled within the amount of time before the meeting begins; and instructions to determine the location to deliver the item based on the distance that is calculated;

instructions to transmit the location to an endpoint device of the recipient; and instructions to control movement of the robot to the location via a position tracking device of the robot to collect location data of the robot.

13. The non-transitory computer readable storage medium of claim 12, wherein the personal data further comprises a daily calorie burn goal and a route preference.

14. The non-transitory computer readable storage medium of claim 12, comprising:

instructions to confirm that the item is delivered to the recipient; and instructions to update the personal data associated with the recipient.

* * * * *